United States Patent [19]

Matsumura et al.

[11] 4,142,058
[45] Feb. 27, 1979

[54] METHOD OF SEPARATING AND PURIFYING METHACRYLIC ACID

[75] Inventors: Hiroshi Matsumura; Takashi Tokutomi; Hideo Matsuzawa, all of Otake, Japan

[73] Assignee: Mitsubishi Rayon Co., Ltd., Tokyo, Japan

[21] Appl. No.: 858,809

[22] Filed: Dec. 8, 1977

[51] Int. Cl.² .................. B01D 3/14; B01D 11/04; C07C 57/04
[52] U.S. Cl. ........................ 562/600; 562/608; 203/43; 203/71; 203/DIG. 21
[58] Field of Search ............... 260/526 N, 541; 203/DIG. 21, 39, 43–46, 15, 71

[56] References Cited
U.S. PATENT DOCUMENTS

| 3,337,740 | 8/1967 | Gray et al. ............... 260/526 N |
| 3,414,485 | 12/1968 | Speed ............... 203/DIG. 21 |
| 3,781,332 | 12/1973 | Sato et al. ............... 260/526 N |

FOREIGN PATENT DOCUMENTS

| 50-11364 | 4/1975 | Japan ............... 260/526 N |
| 1120284 | 7/1968 | United Kingdom ............... 260/526 N |

Primary Examiner—Wilbur L. Bascomb, Jr.
Attorney, Agent, or Firm—Oblon, Fisher, Spivak, McClelland & Maier

[57] ABSTRACT

A method for separating and purifying methacrylic acid is disclosed in which an aqueous solution (A) of methacrylic acid containing acetic acid is brought into contact under counter-current flow with a mixed solvent (B) of methyl methacrylate and toluene in a ratio of from 3 : 2 to 1 : 9 by weight, to extract substantially the whole amount of methacrylic acid in solution (A) into mixed solvent (B); after which the methacrylic acid is separated and purified by distillation.

5 Claims, 4 Drawing Figures ic acid in the
METHOD OF SEPARATING AND PURIFYING METHACRYLIC ACID

BACKGROUND OF THE INVENTION

1. Field of the Invention:

The present invention is related to a method for the separation and purification of methacrylic acid from an aqueous solution of methacrylic acid by a combination of extraction and distillation steps.

2. Description of the Prior Art:

Methacrylic acid may be produced by catalytic oxidation of isobutylene, tertiary butyl alcohol or methacrolein in the vapor phase, and is usually recovered from the reaction gas as an aqueous solution which also contains by-product acetic acid.

Separation of methacrylic acid from this aqueous solution by distillation alone requires many distillation operations, which greatly increases the cost of its recovery and purification. The difficulties of separating methacrylic acid-water systems, acetic acid-water systems, and methacrylic acid-acetic acid systems, respectively, are the cause of this problem.

Therefore, extraction methods have thus far been preferred as the means to separate methacrylic acid from its aqueous solutions, and many extraction solvents have been suggested.

It is well known that esters such as methyl methacrylate are favorable extraction solvents because of their high distribution coefficients $$\left( \frac{\text{acid concentration in organic phase}}{\text{acid concentration in aqueous phase}} \right)$$

for methacrylic acid. However, when acetic acid is also present, it is extracted concurrently with methacrylic acid because the distribution coefficient of acetic acid is high, too. Further disadvantages are that the esters dissolve to a considerable extent in aqueous solution because of their high mutual solubility with water, and that as methacrylic acid is extracted into the esters, the solubility of water in the organic phase also increases.

To avoid these problems, many methods have been suggested, in which a mixed solvent is used containing the esters and hydrocarbons having low mutual solubility with water. These include a method using a mixed solvent of acetic or acrylic ester and toluene for the extraction of acrylic acid from an aqueous solution of acrylic acid (Japanes Pat. No. Sho 41-15569), a method using a mixed solvent of methyl methacrylate and xylene or ethylbenzene (Japanese Pat. No. Sho 49-41413), and a method using a mixed solvent of esters and aliphatic or alicyclic hydrocarbons (Japanese Pat. No. Sho 50-11364).

However, when acetic acid esters or acrylic acid esters are used for the extraction of methacrylic acid, they are slightly hydrolyzed and therefore in the subsequent process, the separation and purification of methacrylic acid from solvent becomes difficult, and in addition, the extractability of methacrylic acid is low. The choice of xylene or ethylbenzene as the hydrocarbon component of a mixed solvent, has the disadvantage that, due to the high boiling point of the solvent, methacrylic acid is easily polymerized by heating when the solvent is to be separated. Being highly polymerizable, methacrylic acid polymerizes to some extent even in the presence of a polymerization inhibitor if it is heated above 90° C., thus making it less suitable for industrial application. Moreover, if the temperature is raised to about the boiling point of xylene or ethylbenzene, methacrylic acid is even more easily polymerized, further diminishing its industrial usefullness. Alicyclic or aliphatic hydrocarbons such as cyclohexane, methylcyclohexane and n-heptane are low in extractability of methacrylic acid, as shown in FIG. 1. Also, when the boiling point of the solvent is too low, separation from methacrylic acid is good, but a great deal of refrigerant is needed for complete recovery of the solvent. Thus, it has been found that in order to avoid heating methacrylic acid above more than 90° C., and to run the solvent-separating process economically after extraction, the solvents to be used must be limited to an extremely narrow boiling point range.

A need, therefore, continues to exist for a method for extracting methacrylic acid from an aqueous solution which also contains acetic acid, wherein the solvent system used has an appropriate boiling point range and a high distribution coefficient while avoiding the solubility problems discussed earlier.

SUMMARY OF THE INVENTION

Accordingly, one object of the invention is to provide an efficient and economical method for separating and purifying methacrylic acid.

Another object of the invention is to provide a method for separating and purifying methacrylic acid minimizes polymerization of the methacrylic acid during its recovery.

Briefly, these objects and other objects of the invention as hereinafter will become readily apparent can be attained by providing a method of separating and purifying methacrylic acid characterized in that an aqueous solution (A) of methacrylic acid which also contains acetic acid is brought into contact under counter-current flow with a mixed solvent (B) of methyl methacrylate and toluene in a ratio of from 3:2 to 1:9 by weight, and methacrylic acid is extracted, then separated by distillation.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein.

DETAILED DESCRIPTION OF THE PREFERRED EMBODIMENTS

Figure 1:
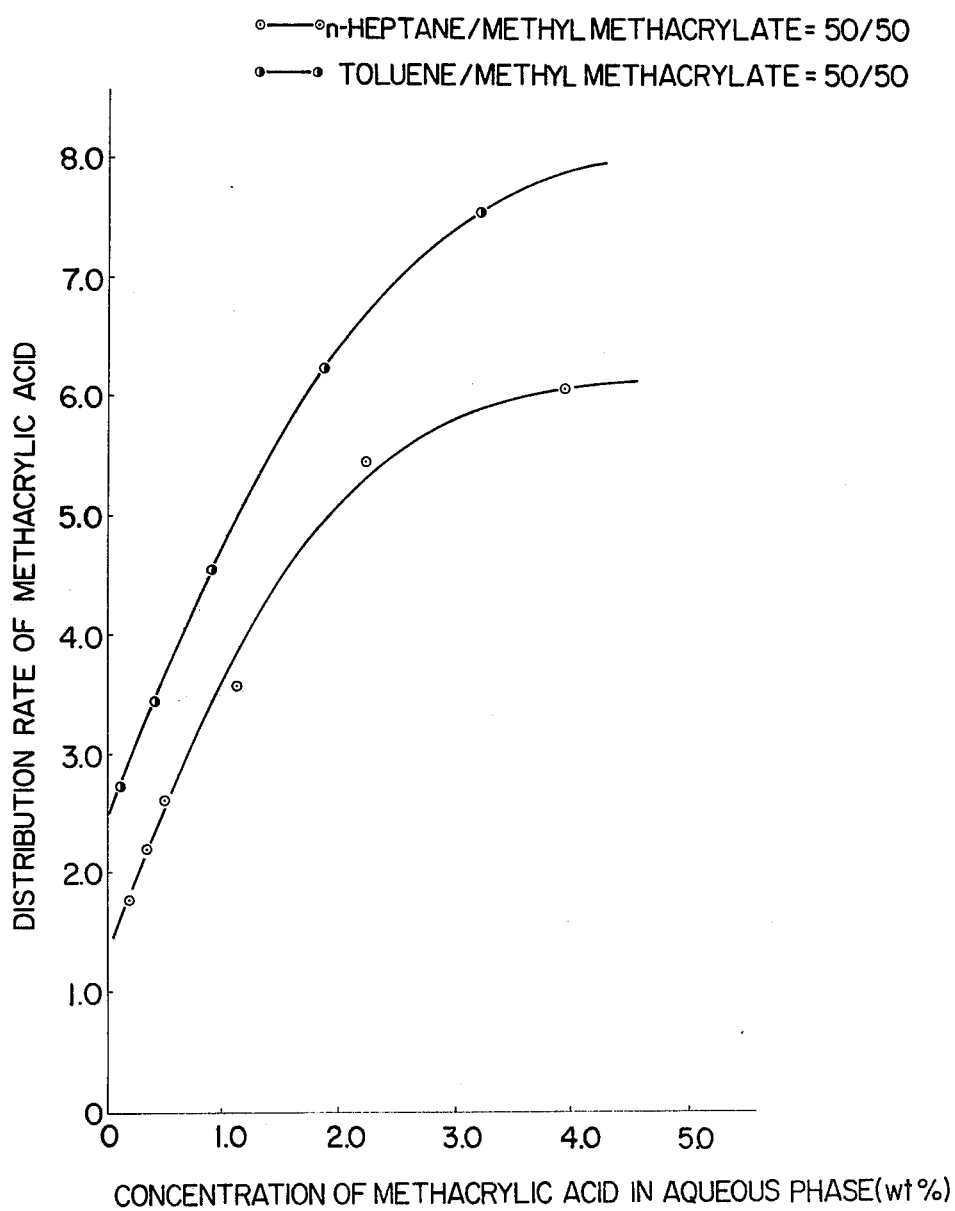
FIG. 1 shows the distribution coefficient of methacrylic acid.

FIG. 1 shows the distribution curve of methacrylic acid in mixed solvent systems containing either n-heptane or toluene and methyl methacrylate and water. Despite the fact that both toluene and n-heptane are 7 carbon hydrocarbons, the astonishingly great difference in distribution coefficient between the two substances increases as the concentration of methacrylic acid in the water phase increases.

In the present invention, the mixing ratio of methyl methacrylate and toluene is in the range of from 3:2 to 1:9 by weight, preferably from 5:5 to 2:8. If the mixing ratio of toluene is below this range, the effect of addition of toluene is insufficient to avoid such problems as transfer of water to the extraction phase, among others. If the mixing ratio of toluene is above this range, the extractability of methacrylic acid is reduced. Mixed solvents falling within the above range are suitable for selectively extracting methacrylic acid alone from an aqueous solution containing methacrylic acid and acetic acid. This is clear from the fact that the distribution coefficient of acetic acid is 0.52 in a solvent containing solely methyl methacrylate, while the coefficient is 0.35 and 0.31 in a mixed solvent containing 50% and 70% by weight of toluene, respectively (values for 20% by weight methacrylic acid in the organic phase). Thus, in the present invention a considerable amount of acetic acid can be separated by extraction, too.

Figure 2:
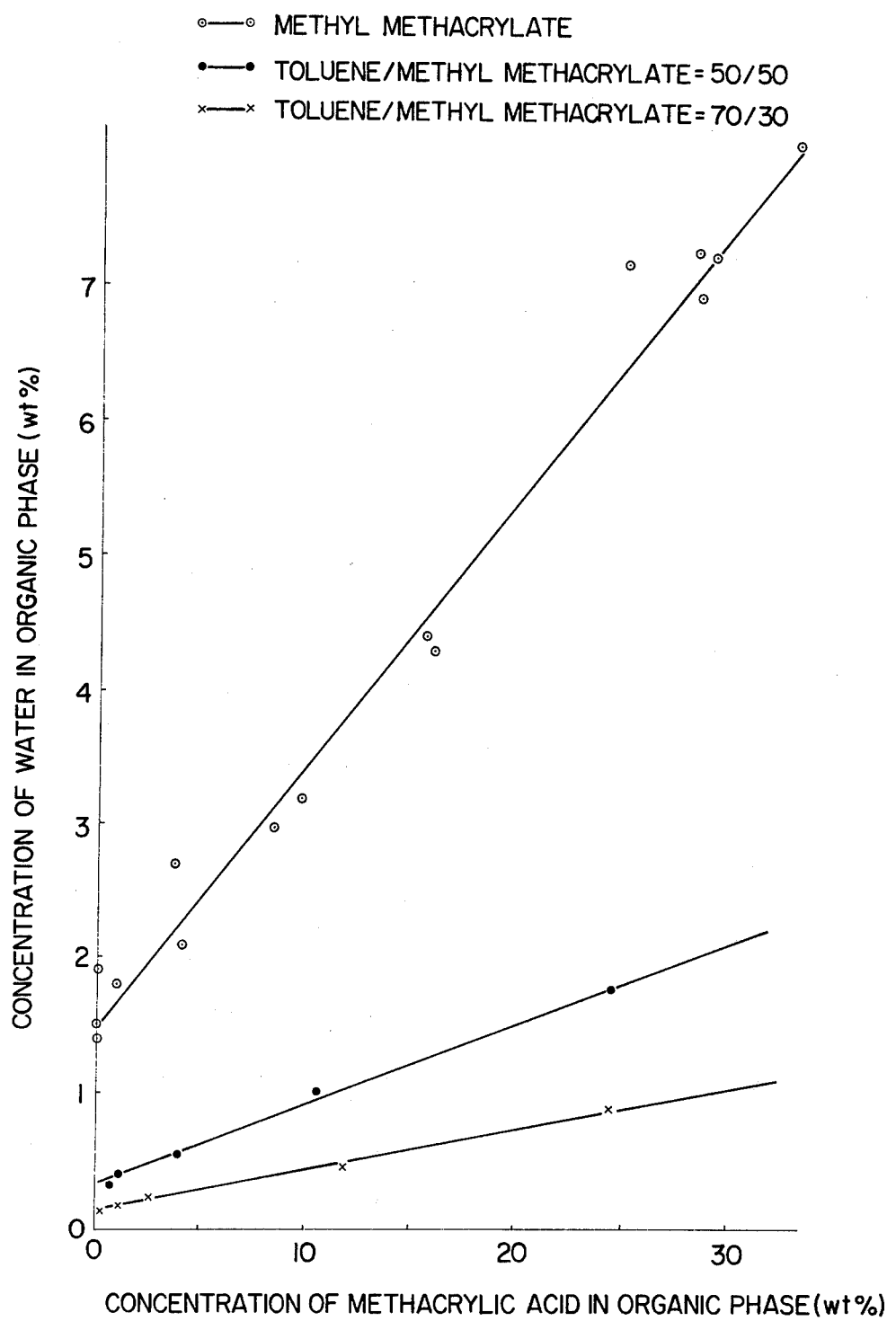
FIG. 2 shows the solubility of water in the organic phase.

FIG. 2 shows the solubility of water in the organic phase. From the figure, it can be found that the solubility of water varies greatly with the mixing ratio of methyl methacrylate and toluene. When mixing ratios according to the present invention are used, no special water removal column need be installed in the solvent-separating stage.

Figure 3:
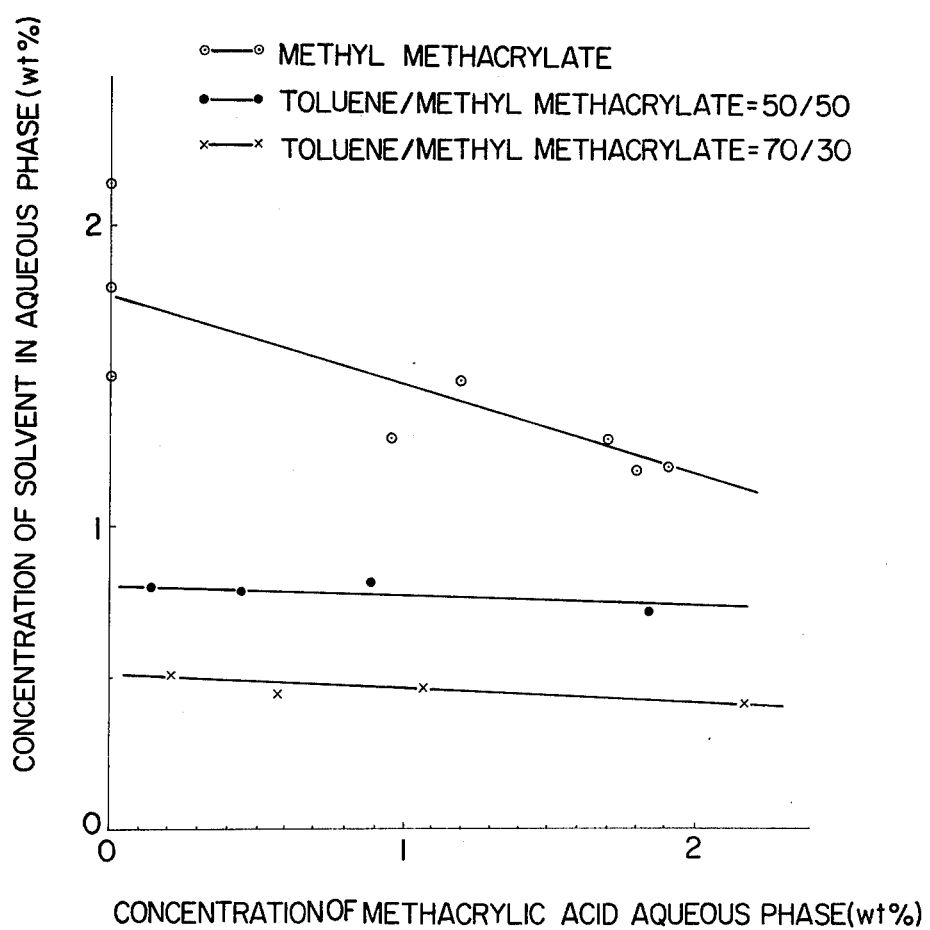
FIG. 3 shows the solubility of solvent in the water phase.

FIG. 3 shows the solubility of the organic solvent in the water phase. From the figure, it is clear that the solubility of the organic solvent depends upon the mixing ratio of methyl methacrylate and toluene. According to the present invention, the solubility of the organic solvent in the water phase can be reduced, and it is also easy to separate the organic solvent from a large amount of water as a methyl methacrylate/toluene/water azeotrope.

The solvent phase (extraction phase) obtained following contact in counter-current flow of an aqueous methacrylic acid solution containing acetic acid with the methyl methacrylate/toluene mixed solvent is sent to a first distilling column. The distillate is recycled to the extracting stage, while the bottoms are sent to a second distilling column and residual solvent, acetic acid and other impurities are distilled and recycled to the extracting stage, while pure methacrylic acid is obtained as the bottoms fraction.

Figure 4:
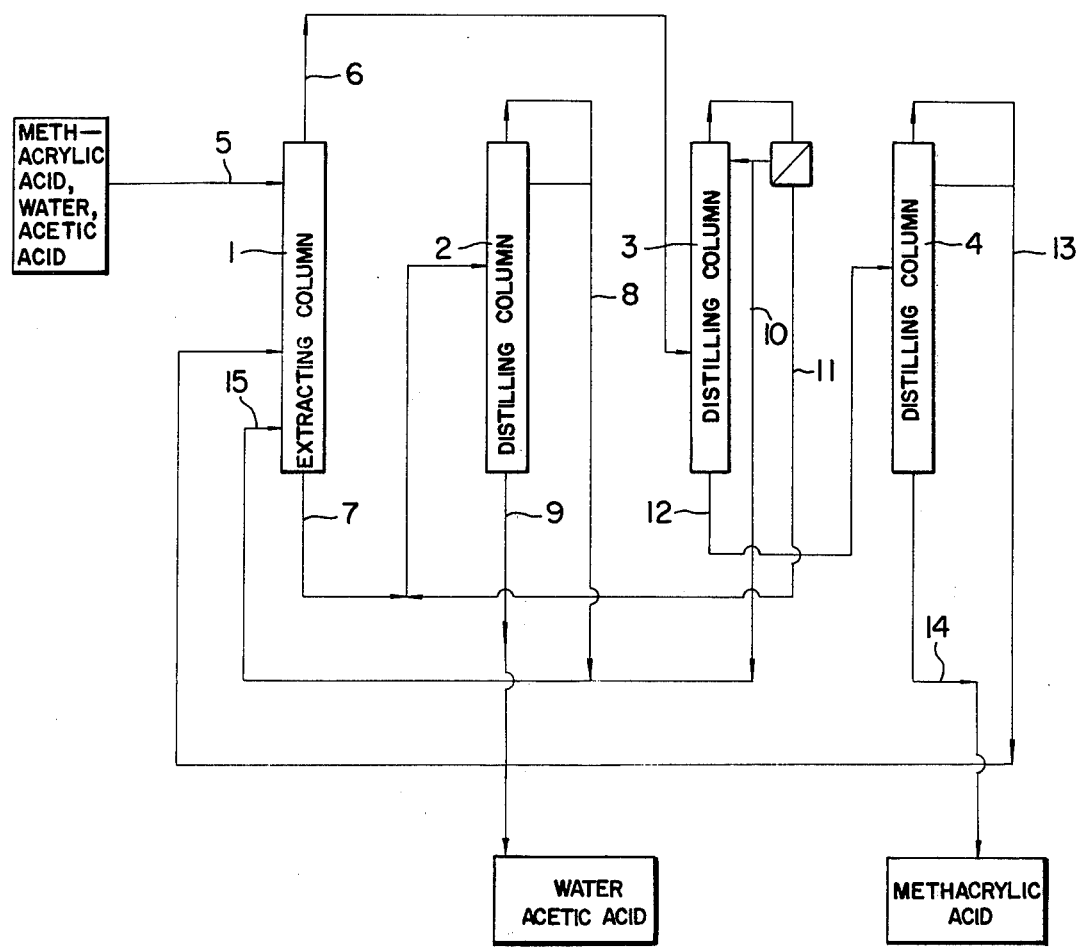
FIG. 4 shows an example of a process employing the method of the present invention.

FIG. 4 shows an example of a separation and purification process for methacrylic acid employing the method of the present invention. The process will be explained below with reference to the drawing.

An aqueous solution of methacrylic acid containing acetic acid is sent via (5) into extracting column (1), while recovered solvent is sent to the column via (15). Counter-current extraction is carried out in column (1), from which an extraction phase is taken out from (6) and an extraction residual phase is taken out from (7).

From the residual phase, solvent is recovered in distilling column (2) and returned via (8) to the extracting column.

From (9), waste water containing acetic acid is removed.

Extraction liquid is sent via (6) to distilling column (3). Distillate is separated into a solvent phase and a water phase, the former being returned via (10) to extracting column (1) and the latter being sent via (11) to distilling column (2).

Bottoms from distilling column (3) are sent via (12) to distilling column (4) where some acetic acid and solvent are separated therefrom.

Distillate from distilling column (4) containing a small amount of methacrylic acid, acetic acid and solvent is sent via (13) to the intermediate stage of extracting column (1).

From (14), the bottoms fraction of purified methacrylic acid is obtained.

In the above process, the recovered extraction solvent contains a very small amount of water and acetic acid. However, it can be recycled to the extracting column without further purification.

In the present invention, various types of extracting columns can be used for the counter-current extraction. It is especially preferable to use extracting columns having a plurality of discs, propellers or other shaped rotors.

Having generally described the invention, a more complete understanding can be obtained by reference to certain specific examples, which are included for purposes of illustration only and are not intended to be limiting unless otherwise specified.

EXAMPLE

An aqueous solution containing 23.5 wt % of methacrylic acid and 8.8 wt % acetic acid was introduced at the top of a 40-stage rotary disc extracting column of 4.6 cm diameter and 76 cm height, at a rate of 3.15 kg/hr. A solvent containing 64.7 wt % of toluene, 27.7 wt % of methyl methacrylate, 4.1 wt % of acetic acid and 1.0 wt % of water was introduced at the bottom of the column at a rate of 1.74 kg/hr to effect counter-current flow extraction at room temperature. An extraction liquid was obtaining having the following compositions:

| | |
|---|---|
| methacrylic acid | 30.8 wt % |
| acetic acid | 3.2 wt % |
| water | 1.5 wt % |
| toluene | 45.5 wt % |
| methyl methacrylate | 18.9 wt % |

As a result, methacrylic acid could be recovered at a rate of 99.3%.

Next, the extraction liquid was distilled in a 10-stage glass Older-show-type distilling column of 3.5 cm diameter at 90 mm Hg, 48° C. head temperature, 85° C. pot temperature and reflux rate of 5, to give a distillate and bottoms having the following compositions:

TABLE 1

| | Flow g/hr | Composition (wt %) | | | | |
| | | Methacrylic Acid | Acetic Acid | Toluene | Methyl Methacrylate | Water |
|---|---|---|---|---|---|---|
| Distillate (organic phase) | 1616.0 | 0.18 | 3.0 | 67.7 | 28.1 | 1.0 |
| Distillate (water phase) | 29.3 | 0.50 | 24.50 | 0.14 | 1.81 | 73.0 |
| Bottoms | 885.0 | 87.7 | 2.8 | 6.7 | 2.8 | — |

Next, the bottoms shown in Table 1 were distilled in a 25-stage glass Oldershow-type distilling column of 3.5 cm diameter at 20 mm Hg, 50° C. head temperature, 88° C. pot temperature, and reflux rate of 5, to give a bottoms fraction consisting of pure methacrylic acid and a distillate having the following composition.

TABLE 2

|  | Flow g/hr | Composition (wt %) | | | |
| --- | --- | --- | --- | --- | --- |
|  |  | Methacrylic Acid | Acetic Acid | Toluene | Methyl methacrylate |
| Distillate | 149.4 | 27.2 | 16.7 | 39.6 | 16.5 |
| Bottoms | 735.6 | more than 99.8 | — | — | — |

COMPARISON EXAMPLE 1

Under the same conditions as in the above Example, except that n-heptane was used instead of toluene, counter-current flow extraction was carried out at room temperature, to obtain methacrylic acid at the rate of 95.7%. Compared with the toluene-containing solvent, the extractability was substantially worse.

COMPARISON EXAMPLE 2

Under the same conditions as in the Example, except that ethylbenzene was used instead of toluene, counter-current extraction and distillation of the extraction liquid (recovery of solvent) were carried out, and it was found that a distilling column having 40 stages was needed for the methacrylic acid-purifying distillation and that the temperature of the still pot reached 94° C. at a pressure of 20 mm Hg, thus showing the difficulties of industrial application.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for separating and purifying methacrylic acid which comprises the steps of:
   bringing an aqueous solution of methacrylic acid which also contains acetic acid into contact under counter-current flow with a mixed solvent containing methyl methacrylate and toluene in a ratio of from 5:5 to 1:9 by weight, to extract substantially all said methacrylic acid into said mixed solvent in an extraction phase; and
   separating and purifying said methacrylic acid by distillation of said extraction phase.

2. The method of claim 1, wherein said distillation comprises the steps of:
   distilling said extraction phase in a first distilling column;
   recycling the distillate from said first distilling column to the counter-current extraction stage;
   conducting the bottoms from said first distilling column to a second distilling column and distilling said bottoms;
   recycling the distillate from said second distilling column to the counter-current extraction stage; and
   isolating pure methacrylic acid as the bottoms fraction from said second distilling column.

3. The method of claim 1, wherein said ratio of methyl methacrylate and toluene is from 5:5 to 2:8 by weight.

4. The method of claim 1, wherein said counter-current extraction is performed in an extracting column having a plurality of rotors therein.

5. The method of claim 1, wherein said distillation is performed at a pot temperature lower than 90° C.

* * * * *

UNITED STATES PATENT AND TRADEMARK OFFICE
CERTIFICATE OF CORRECTION

PATENT NO. : 4,142,058

DATED : February 27, 1979

INVENTOR(S) : Hiroshi Matsumura et al

It is certified that error appears in the above—identified patent and that said Letters Patent is hereby corrected as shown below:

Column 4, line 48, delete "reflux rate of 5" and insert --reflux rate of 0.5--.

Signed and Sealed this

Fourteenth Day of April 1981

[SEAL]

Attest:

RENE D. TEGTMEYER

Attesting Officer   Acting Commissioner of Patents and Trademarks